United States Patent
Givler et al.

(10) Patent No.: US 6,945,945 B2
(45) Date of Patent: Sep. 20, 2005

(54) FLACCID UPPER EXTREMITY POSITIONING APPARATUS

(75) Inventors: Victoria Givler, Albuquerque, NM (US); Paul Mohr, Albuquerque, NM (US)

(73) Assignee: Givmohr Corporation, Albuquerque, NM (US)

( * ) Notice: Subject to any disclaimer, the term of this patent is extended or adjusted under 35 U.S.C. 154(b) by 217 days.

(21) Appl. No.: 09/895,373

(22) Filed: Jun. 28, 2001

(65) Prior Publication Data

US 2002/0007133 A1 Jan. 17, 2002

Related U.S. Application Data

(60) Provisional application No. 60/214,842, filed on Jun. 28, 2000.

(51) Int. Cl.$^7$ .................................................. A61F 5/00
(52) U.S. Cl. .................................. 602/20; 602/4; 602/5
(58) Field of Search ........................... 602/4, 5, 20, 21, 602/12, 19, 61, 62, 64; 128/876–878, 881, 869; 2/24, 44

(56) References Cited

U.S. PATENT DOCUMENTS

| | | | | |
|---|---|---|---|---|
| 2,187,323 A | * | 1/1940 | Kelton et al. .................. | 602/20 |
| 2,358,551 A | * | 9/1944 | Beaton ........................ | 224/259 |
| 3,000,378 A | | 9/1961 | Zieman | |
| 3,338,236 A | * | 8/1967 | McLeod, Jr. .................. | 602/19 |
| 3,404,680 A | * | 10/1968 | Guttman et al. ............... | 602/4 |
| 3,815,588 A | | 6/1974 | Klausner ...................... | 128/77 |
| 4,188,944 A | * | 2/1980 | Augustyniak ................. | 602/20 |
| 4,598,703 A | | 7/1986 | Lindemann ................... | 128/94 |
| 4,716,895 A | | 1/1988 | Marques et al. ............... | 128/94 |
| 4,834,082 A | | 5/1989 | Ghadiali ...................... | 128/94 |
| 5,203,763 A | | 4/1993 | Lajiness-O'Neill ............ | 602/4 |
| 5,358,470 A | * | 10/1994 | Johnson ....................... | 602/20 |
| 5,358,471 A | | 10/1994 | Klotz .......................... | 602/21 |
| 5,403,268 A | | 4/1995 | Clement ....................... | 602/20 |
| 5,520,620 A | * | 5/1996 | Johnson ........................ | 602/5 |
| 5,558,626 A | * | 9/1996 | Holtzman et al. ............. | 602/4 |
| 5,628,725 A | | 5/1997 | Ostergard ..................... | 602/62 |
| 5,857,990 A | | 1/1999 | Maas .......................... | 602/62 |
| 5,867,826 A | * | 2/1999 | Wilkinson | |
| 6,099,489 A | * | 8/2000 | Herzberg et al. .............. | 602/4 |
| 6,106,493 A | | 8/2000 | Rozell ......................... | 602/20 |
| RE36,869 E | * | 9/2000 | Ewen | |
| 6,421,834 B2 | * | 7/2002 | Kester | |
| 6,464,656 B1 | * | 10/2002 | Salvucci et al. ............... | 602/4 |

FOREIGN PATENT DOCUMENTS

| | | | | | |
|---|---|---|---|---|---|
| DE | 3936232 | * | 5/1991 | ................... | 602/21 |
| EP | 0198482 | * | 4/1986 | | |
| NR | 89148 | * | 4/1957 | .................... | 602/4 |

OTHER PUBLICATIONS

Page 390 from a Sammons Preston catalog showing several types of shoulder supports. Publication date unknown.
Page F47 from an Alimed catalog chowing the shoulder sling covered by U.S. patent No. 5,403,268. Publication date unknown.

* cited by examiner

Primary Examiner—Justine R Yu
Assistant Examiner—Fenn C. Mathew
(74) Attorney, Agent, or Firm—Roberts, Abokhair & Mardula, LLC

(57) ABSTRACT

A positioning apparatus for facilitating normal motor return by supporting a flaccid (non-innervated muscles) arm in a functional position. The arm is held in a dependant position with the scapula held in depression, retraction and neutral rotation. The shoulder joint is held in neutral rotation or slight external rotation and mild extension with the arm held at the side of the body. The elbow is held in less than 30 degrees flexion. The wrist is held in neutral deviation and neutral to mild extension. The fingers are in slight flexion and the thumb is in moderate abduction and opposition.

39 Claims, 4 Drawing Sheets

Fig. 1

FLACCID UPPER EXTREMITY POSITIONING APPARATUS

CROSS-REFERENCE TO RELATED APPLICATIONS

This application claims priority of U.S. Provisional Patent Application Ser. No. 60/214,842, entitled "Upper Extremity Support", to Victoria Givler and Paul Mohr, filed on Jun. 28, 2000, and the specification thereof is incorporated herein by reference.

BACKGROUND OF THE INVENTION

1. Field of the Invention (Technical Field)

The invention described and claimed herein is generally related to an upper extremity or arm supportive sling or apparatus. More specifically, this invention is related to an upper extremity supportive apparatus that provides support and protection to the flaccid upper extremity of the human body.

Cerebral vascular accident (CVA) is a devastating event that brings with it a wide variety of impairments. The deficits arising from even a small CVA can affect every system in the body. Physically, the most noticeable system affected is the musculoskelatal system. Following CVA, the muscles of the involved side have the daunting task of functioning with an altered nervous system. Rehabilitation is often frustrating and functional returns may be minimal. Nowhere is this seen or felt more than in the upper extremity.

A flaccid or low tone upper extremity is a common finding in individuals following a CVA, and its rehabilitation is crucial in the recovery process. A flaccid upper extremity presents a challenge to the treating therapist because the protection necessary for the extremity involved often hinders its functional return.

Upper extremity positioning and slings are often used to protect the upper extremity. There are several different ambulatory upper extremity supports used in stroke rehabilitation. All of these slings are designed to support the arm, but few actually reduce subluxation and none of them support the arm in a functional position. Therefore, support of the hemiplegic limb while in the upright position remains controversial.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Approximately 600,000 individuals are diagnosed with cerebral vascular accidents ("CVA") annually in the United States. Many of these individuals have temporary or permanent hemiparesis. In addition to the obvious loss of function on the involved side, these individuals run the risk of mechanical injury to the involved upper extremity in addition to the deficits resulting from the neurological insult of the CVA, including damage to the rotator cuff musculature and associated cognitive neglect, and damage to the shoulder and arm resulting from external forces to an unprotected and uncontrolled flaccid arm. In addition, positioning of the flaccid arm for long periods of time (commonly, internal rotation at the shoulder by placing forearm across stomach) can result in shortening of the soft tissue crossing the joint, resulting in significantly reduced joint range of motion. This is an absolutely tragic situation for those who experience eventual return of motor function in the upper extremity.

The above mentioned risks of mechanical injury to the involved upper extremity are easily controlled with proper support and positioning while the individual is seated. While performing standing tasks and ambulating, the same risks can be effectively controlled with the skill of a well-trained therapist and assistive devices. As the individual progresses toward independent function, the controls on the risks of mechanical injury are lost. Products on the market today do not effectively control all the above mentioned risks to mechanical injury to the involved flaccid upper extremity once the individual is progressing toward independent function.

The following are slings available in the prior art. However, these slings do not provide appropriate positioning or control of a flaccid upper extremity.

The Harris Hemi-Arm Sling is a sling centered at the front part of the body. This sling holds the arm in an inappropriate position for a flaccid upper extremity.

The AliMed Hemi Shoulder Sling, U.S. Pat. No. 5,403,268, is a sling with a shoulder harness and upper arm portion. The sling is complicated to put on; and the arm cuff is intended to reduce subluxation, but instead it creeps up the arm and is ineffective. Further, it lacks distal arm control and does not hold the arm in a functional position.

The Shoulder Saddle sling, sold by AliMed, Inc., provides a shoulder harness and a lower arm portion. However, the cuff on the lower arm portion rides up on the arm and does provide effective reduction of shoulder subluxation. Further, it does not provide a weight-bearing member for the wrist and hand and does not control the elbow and wrist joints.

U.S. Pat. No. 4,834,082 entitled "Arm Sling for Stroke Patients," to Ghadiali, is directed to an arm sling with a back shoulder harness. This sling holds the arm in an inappropriate position for a flaccid upper extremity.

U.S. Pat. No. 4,716,895, entitled "Arm Sling," to Marques et al., has a shoulder portion, an upper arm portion and a lower arm portion. It further has an attachment to the user's belt. This sling holds the arm in an inappropriate position for a flaccid upper extremity.

U.S. Pat. No. 5,857,990, entitled "Orthopedic Garment for Dynamic Scapular and Acromio-Clavicular Stabilization, Including Dynamically Enhancing Proper Posture," to Maas; U.S. Pat. No. 5,628,725, entitled "Shoulder Stabilizer Methods," to Ostergard; and U.S. Pat. No. 6,106,493, entitled "Shoulder Stabilizer," to Rozell; are all directed to shoulder sling systems. These slings are used for orthopedic problems; are not designed to reduce neurological subluxation; do not facilitate neurological return; and do not control a flaccid upper extremity in a functional position.

U.S. Pat. No. 4,598,703, entitled "Hemi-Arm Sling," to Lindemann, is directed to a sling with a shoulder harness and an upper arm portion. This sling is complicated to put on; the arm cuff, which is intended to reduce subluxation, actually creeps up the arm and is ineffective; it lacks distal arm control; and there is no control of functional arm position.

U.S. Pat. No. 3,815,588, entitled "Apparatus and Methods Relating to Support of the Forearm," to Klausner, is directed to a sling with a shoulder portion and a lower arm and hand portion. The sling does not hold the arm in an appropriate position for a flaccid upper extremity.

U.S. Pat. No. 5,203,763, entitled "Dynamic Sling," to Lajiness-O'Neill, is directed to a shoulder support and two opposing upper arm supports. It does not hold the arm in an appropriate position for a flaccid upper extremity nor does it provide for weight bearing wrist and hand control.

The present invention, in contrast to the prior art, provides proper positioning for a flaccid upper extremity; holds the arm in a functional position; provides effective reduction of neurological subluxation; provides a weight bearing member for the wrist and hand; controls the elbow and wrist joints; facilitates neurological return; and is easy to put on and adjust and use.

SUMMARY OF THE INVENTION (DISCLOSURE OF THE INVENTION)

The present invention relates to a sling apparatus. The sling comprises a shoulder harness removably positionable atop one shoulder of a user; a hand section (on the same side of the user's body as the shoulder harness) removably positionable in the user's hand; and an anterior arm section (removably positionable on the same side of the user's body as the shoulder harness and the hand section) connecting the shoulder harness to the hand section.

The sling preferably further comprises a removably positionable posterior arm section, that is adjustable and has and elastic member. Likewise, the anterior arm section is preferably adjustable and has an elastic member.

The preferred shoulder harness also has a bilateral shoulder and contralateral axilia section. This shoulder harness forms a cross at a posterior center of the user's back and is preferably adjustable. This shoulder harness provides bilateral scapular retraction, scapular depression and thoracic spine extension.

The preferred hand section comprises a rigid object, preferably removably positionable in a palmar surface of the user's hand. The object can be configured to user's palm. The hand section can be a cylindrical or tubular configuration. The hand section can be padded. The hand section preferably comprises at least one adjustment to control ulnar deviation and radial deviation.

The sling preferably further comprises an elbow section removably positionable adjacent or at the user's elbow. This elbow section is connected to the anterior arm section and posterior arm section. The elbow section positions the user's arm, reduces shoulder subluxation and adjusts internal and external rotation of the user's shoulder. The elbow section is preferably adjustable.

The sling apparatus preferably further comprises a wrist section disposed between the anterior arm section and the hand section. The wrist section preferably crosses over the user's wrist and is adjustable.

A primary object of the present invention is to provide an effective sling that supports a flaccid upper extremity.

Primary advantages of the present invention are that it is easy to put on and use, it provides optimal positioning of the upper extremity and it facilitates neuromus ulnar return.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DESCRIPTION OF THE PREFERRED EMBODIMENTS (BEST MODES FOR CARRYING OUT THE INVENTION)

It is believed that early, proper support of a flaccid upper extremity leads to decreased subluxation, increased potential for motor return, and improved balance and upright mobility skills. The sling of the present invention supports the upper extremity in a functional position, reduces shoulder subluxation and provides weight-bearing through the involved side to increase proprioception and normalize tone. This support provided by the present invention allows for improved movement quality and increased function. The sling is to be used in upright activities including walking.

The present invention comprises a flaccid upper extremity supportive apparatus comprising:

(1) A hand section (e.g. made of vinyl) designed to distribute weight of the upper extremity across the palmer surface of the hand, adjustable for optimum wrist positioning (flexion/extension and ulnar/radial deviation).

(2) An elastic arm piece providing dynamic compressive forces through the wrist, elbow, and shoulder joints and the long bones of the arm (to facilitate neuromuscular return), with adjustments at the elbow (e.g. hook and loop or Velcro®), chest (e.g. buckle) and back (e.g. buckle) to allow optimal positioning and protection of the upper extremity (shoulder subluxation reduction, joint compression at elbow and wrist, shoulder internal/external rotation, and elbow flexion/extension).

(3) A webbed shoulder harness designed to distribute weight of the involved upper extremity across the shoulders and under the contralateral axilla and to facilitate proper posture in upper trunk and shoulders (bilateral scapular retraction and thoracic spine extension) adjustments at back (e.g. hook and loop), chest (e.g. buckle) and back (e.g. buckle).

Figure 1:
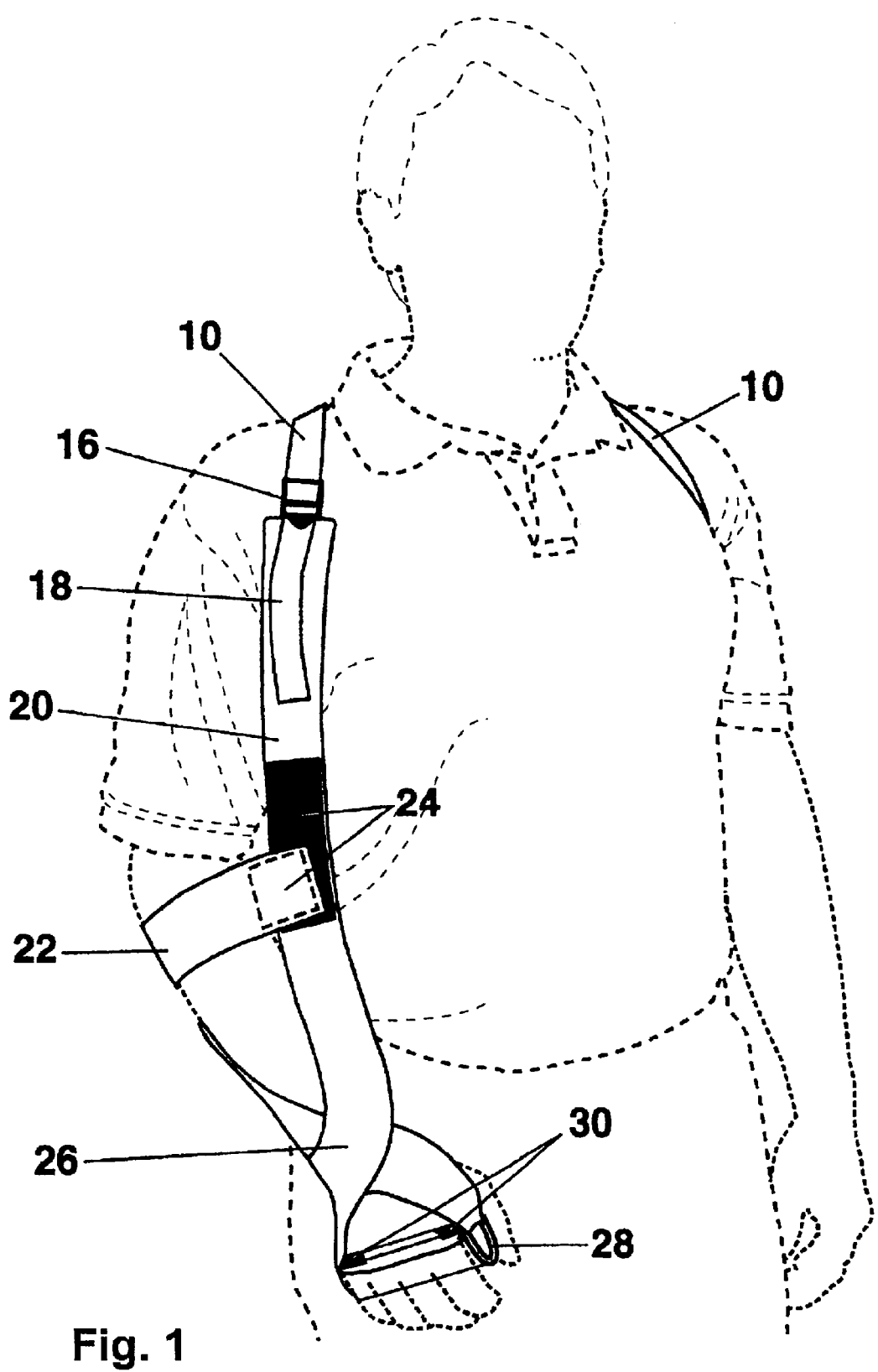
FIG. 1 is a front view of the preferred embodiment of the sling of the present invention in use.
Figure 2:
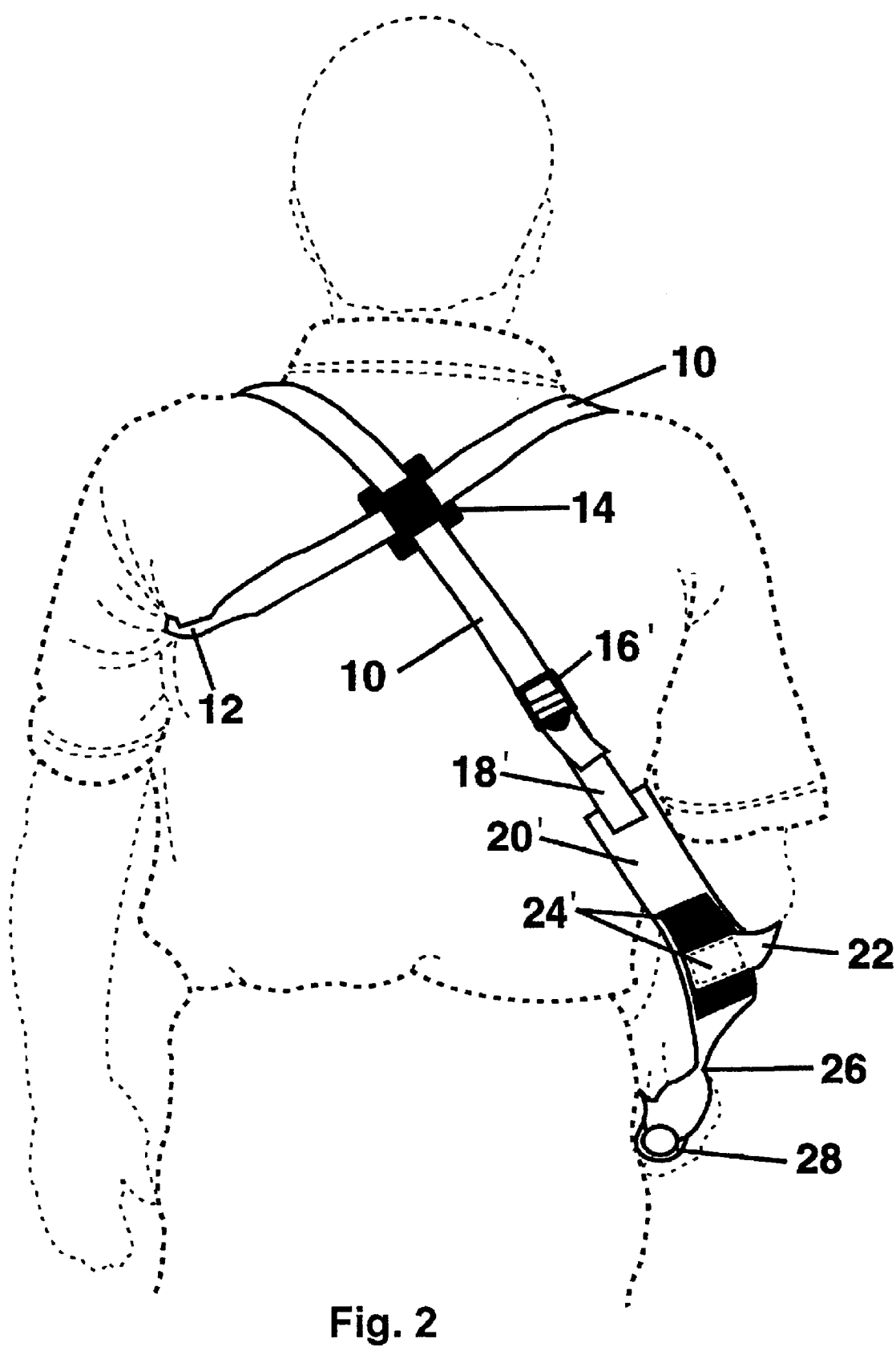
FIG. 2 is a back view of the sling of the FIG. 1 embodiment.
Figure 3:
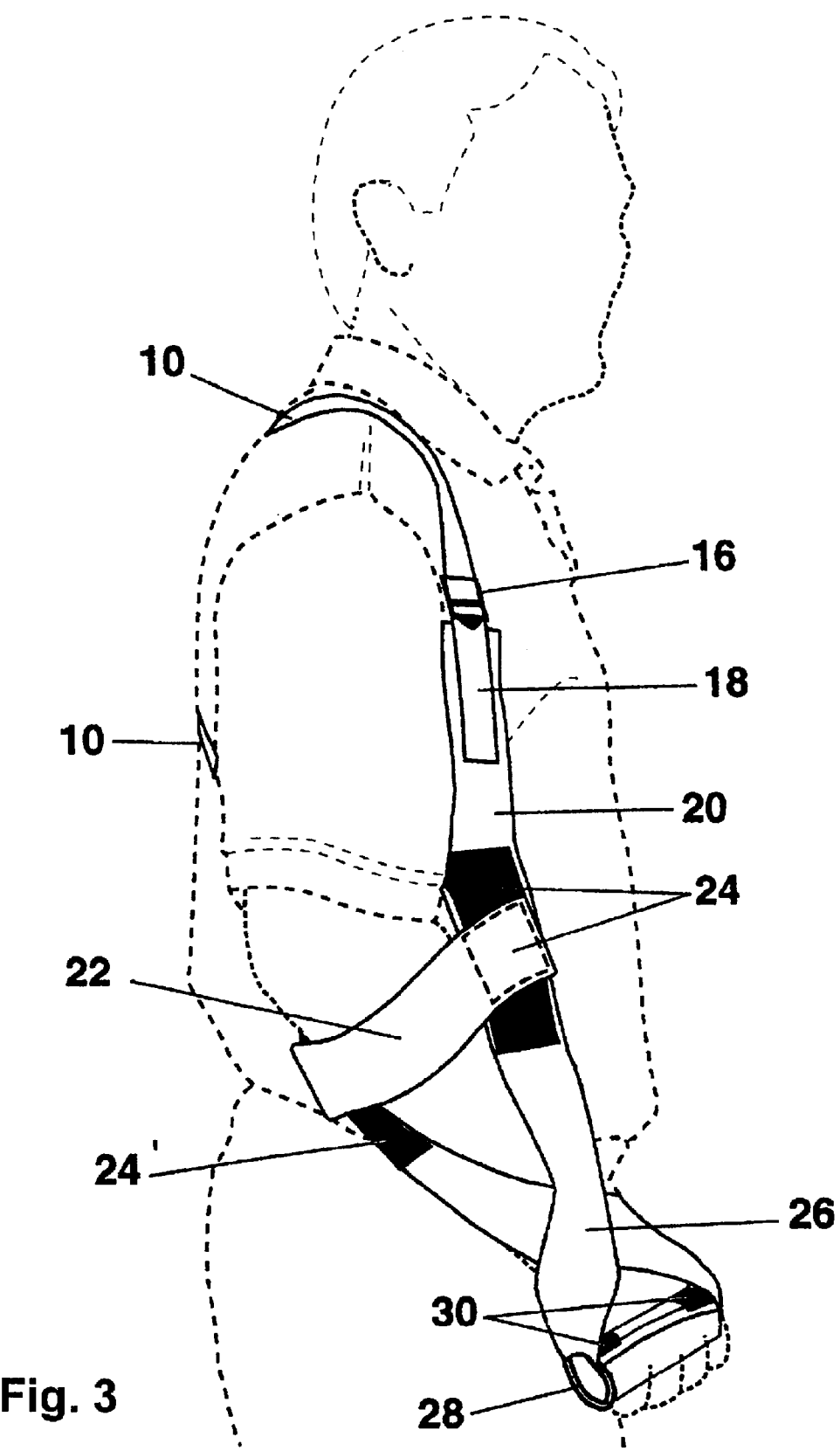
FIG. 3 is an involved right side view of the sling of the FIG. 1 embodiment.
Figure 4:
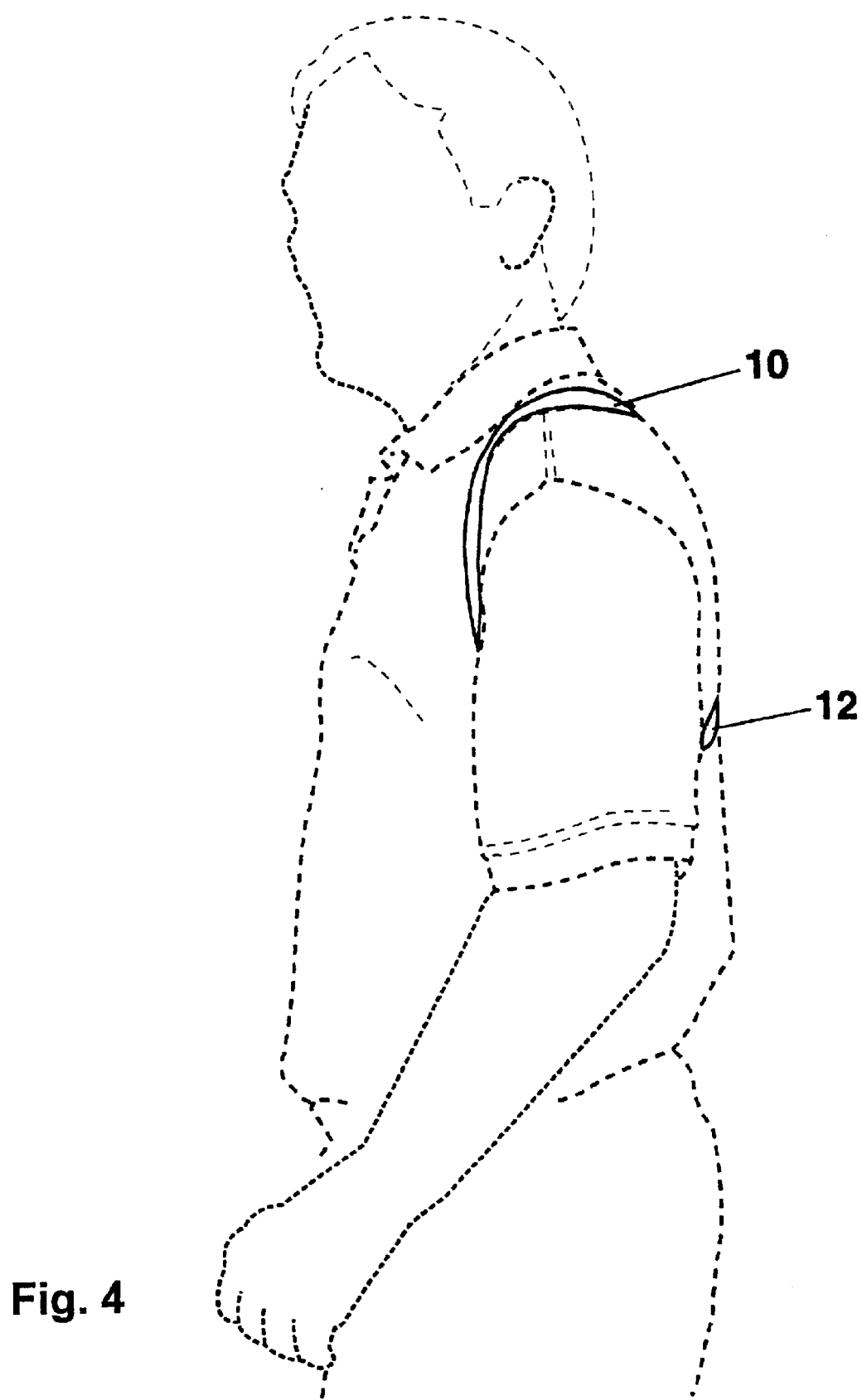
FIG. 4 is an uninvolved left side view of the sling of the FIG. 1 embodiment.

Referring to FIGS. 1–4, a preferred embodiment of the flaccid upper extremity positioning apparatus or sling of the present invention is shown. The sling shown is for a right upper extremity. Obviously, the sling can be reversed for a left upper extremity.

As shown in FIGS. 1–4, shoulder harness 10, preferably made of webbing (e.g. one-inch wide polypropylene), is connected to adjustment strap 18 via buckle 16 (e.g. made of plastic) to elastic arm piece 20, anteriorly, and connected to adjustment strap 18', via buckle 16' (e.g. made of plastic) to elastic arm piece 20', posteriorly.

Shoulder harness 10 distributes the weight of an involved upper extremity across bilateral shoulders and under the contralateral axilla, and facilitates improved posture through bilateral scapular retration and scapular depression, and thoracic spine extension. Proper positioning and weight distribution is achieved through posterior adjustment 14 (e.g. four-tab buckle). Axillary piece 12 is folded for improved comfort. In an alternate embodiment, an alternative shoulder harness provides increased stabilization of the scapula on the posterior thoracic wall (through modification of harness positioning/construction).

Axillary piece 12 is formed by folding of shoulder harness 10 webbing to provide increased comfort to the user. In an alternate embodiment, an alternative axillary piece is made of a padded material. In a further alternative embodiment, an alternative axillary piece is made of low profile material.

Posterior adjustment 14 (e.g. four-tab buckle) allows for proper distribution of involved upper extremity weight across the bilateral shoulders and contralateral axilla.

Buckles 16, 16' with a double bar slide, two each, connects shoulder harness 10 to adjustment strap 18, 18' anteriorly and posteriorly.

Adjustment straps 18, 18' are used to adjust tension through elastic arm pieces 20, 20', anteriorly and posteriorly for proper positioning of the involved upper extremity, reduction of shoulder subluxation, and proper adjustment of shoulder internal and external rotation.

Elastic arm piece 20, 20' preferably made of wide poly-elastic webbing (e.g. two-inch), is connected proximally to shoulder harness 10, via anterior and posterior adjustment straps 18, 18' and anterior and posterior buckles 16, 16' and connected distally to hand piece 28, via adjustable (e.g. hook and loop) hand piece connection 30. This configuration is designed to provide proper positioning to the flaccid upper extremity and dynamic compressive support through the wrist, elbow and shoulder joints of the involved upper extremity. Elbow extension is controlled by elastic elbow piece 22, preferably made of wide poly-elastic (e.g. two-inch), connected to elastic arm strap 20, 20' via anterior and posterior adjustable connection (e.g. hook and loop) 24, 24'. Wrist extension is controlled by wrist cross 26. Wrist ulnar and radial deviation is controlled by hand piece connection 30 (e.g. hook and loop).

Hand piece 28 is preferably made of a cylinder or vinyl tubing (e.g. vinyl or plastic) sized and contoured to accommodate the palmer surface of the hand. Hand piece 28 is designed to distribute the weight of the upper extremity across the palmer surface of the hand, and can be adjusted (e.g. by hook and loop) to hand piece connection 30 to control ulnar and radial deviation.

In an alternate embodiment, there is an elastic arm piece comprising heavy-duty elastic material which increases the life of the sling. An alternate hand piece comprises a controlled and padded rigid material that provides greater support, decreased potential for skin breakdown, and increased comfort to the palmer surface of the hand.

In a further alternate embodiment of the present invention, the arm piece comprises non-elastic webbing to provide static compressive forces through the wrist, elbow and shoulder. An alternate hand piece comprises perforated material that provides increased airflow at the palmer surface of the hand and decreased potential for skin breakdown.

In a further alternate embodiment of the present invention, the wrist cross connection 26 is adjustable and comprises a connection (e.g. hook and loop) to provide increased control of wrist position. This alternate embodiment includes a hand piece in which the diameter is preferably significantly reduced or eliminated to accommodate hand function.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

EXAMPLE 1

Three case studies have been conducted with the present invention. The first research project was a study to determine the effects of the upper extremity weight bearing sling on the gait of post CVA patients with flaccid upper extremities. It was concluded that there was a statistically significant increase in the step length of the non-hemiplegic side on the subject who wore the sling. Because of the upper extremity weight bearing sling, the subject was able to spend more time in stance phase on the involved side thus increasing the step length of the uninvolved side. The natural position of the upper extremity provided by the sling enabled the patient to move in a more normal pattern during upright activities. Allowing the upper extremity its normal position during gait keeps the center of mass centered over the base of support which is required for optimum balance.

The second research project was on the effects of the present invention on reducing both horizontal and vertical subluxation. The study reviewed types of slings available and what were the ideal characteristics of slings to support the flaccid upper extremity. It was found that the incidence of subluxation in CVA survivors varies from 12%–73%. If shoulder subluxation is left untreated, complications such as distension of the capsule, stretching of surrounding musculature, limited mobility, shoulder hand syndrome, subacromial impingement, interference with functional activities, and impairing return of upper limb function occur. Use of the sling of the present invention prevented these injuries.

A study was also conducted which included proper positioning of the humeral head in the glenoid fossa, some humeral abduction, external rotation, elbow extension, neutral wrist, unobstructed hand function, abduction of fingers, encouragement of scapular depression and retraction. The sling of the present invention also provides comfort, cosmetic appeal, snug fit without skin breakdown and the capacity of permit active or passive ROM.

Three anterior/posterior view radiographs were taken of three individuals with a flaccid upper extremity and the uninvolved shoulder; without the sling of the present invention, and with the sling of the present invention. The study found that the present invention reduced subluxation in addition to its other functions. The study by Smith concluded that the sling of the present invention meets the criteria on the "Checklist for Prescription of Slings." It also provided forearm support, and was successful in decreasing subluxation vertically and horizontally without overcorrecting. The present invention is successful by the above criteria and promotes weight bearing in anatomical and functional positions.

The third project was a study on the effects of the present invention on function following stroke. The purpose of this study was to determine the effectiveness of a custom-made upper extremity sling on return of functional activity. The measurement tools used were the Functional Independence Measure and the Fugl-Meyer Assessment. Four subjects who had sustained a CVA within the past year participated in the study. All subjects were admitted to a rehabilitation facility and had a flaccid upper extremity. Subjects were placed in either a sling or non-sling group and all subjects received standard therapy using the Neuro-Developmental Treatment technique. Pre- and post-test measures of functional abilities were conducted at two-week intervals. Subjects wearing the present invention improved their UE function, locomotion, and self-care skills while subjects without the present invention showed no UE improvement. The study concluded that the present invention leads to greater and more timely functional recovery of the flaccid UE.

In conclusion, based on the results of studies, the present invention reduces shoulder subluxation, increases stance time on the hemiplegic side thus increasing the step length, and leads to greater and more timely functional recovery.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A sling apparatus for supporting a flaccid arm of a user, the sling apparatus comprising:
   a shoulder harness removably positionable atop at least one shoulder of the user;
   a hand section removably positionable in a hand of the user, the hand section supporting weight of the arm across a surface of the hand;
   an arm section removably positionable against the arm of the user, the arm section connecting the shoulder harness to the hand section; and
   the shoulder harness, the hand section, and the arm section being disposed in such a manner that the arm is supported so that the wrist joint, the elbow joint, and the shoulder joint are all in compression.

2. The sling apparatus of claim 1, wherein the arm section comprises a posterior arm strap, removably positionable to rest against a posterior surface of the arm and a medial surface of the forearm, and an anterior arm strap, removably positionable to rest against an anterior surface of the arm and a lateral surface of the forearm.

3. The sling apparatus of claim 2 wherein the posterior arm strap is adjustable.

4. The sling apparatus of claim 2 wherein the posterior arm strap comprises an elastic member.

5. The sling apparatus of claim 2 wherein the anterior arm strap is adjustable.

6. The sling apparatus of claim 2 wherein the anterior arm strap comprises an elastic member.

7. The sling apparatus of claim 2 further comprising an elbow section removably positionable adjacent or at the user's elbow, the elbow section connected to the anterior arm strap and the posterior arm strap.

8. The sling apparatus of claim 7 wherein the elbow section positions the user's arm and reduces shoulder subluxation.

9. The sling apparatus of claim 7 wherein the elbow section is adjustable.

10. The sling apparatus of claim 2 wherein the hand section comprises a wrist section comprises disposed at a junction of the anterior and posterior arm straps where the arm straps connect to the hand section.

11. The sling apparatus of claim 10 wherein the wrist section is removably positionable to fit against a dorsal surface of the wrist of the user.

12. The sling apparatus of claim 11 wherein the wrist section is adjustable.

13. The sling apparatus of claim 1 wherein the shoulder harness comprises a bilateral shoulder and contralateral axilla section.

14. The sling apparatus of claim 13 wherein the shoulder harness forms a cross at a posterior center of the user's back.

15. The sling apparatus of claim 14 wherein the cross of the shoulder harness is adjustable.

16. The sling apparatus of claim 13 wherein the shoulder harness provides bilateral scapular retraction, scapular depression and thoracic spine extension.

17. The sling apparatus of claim 1 wherein the hand section is removably positionable to fit against a palmar surface of the users hand.

18. The sling apparatus of claim 17 wherein the hand section comprises an object configured to the palm of the user's hand.

19. The sling apparatus of claim 1 wherein the hand section comprises a rigid object.

20. The sling apparatus of claim 1 wherein the hand section is shaped in a cylindrical or tubular configuration.

21. The sling apparatus of claim 1 wherein the hand section is padded.

22. The sling apparatus of claim 1 wherein the hand section comprises at least one adjustment to control ulnar deviation.

23. The sling apparatus of claim 1 wherein the hand section comprises at least one adjustment to control radial deviation.

24. The sling apparatus of claim 1 wherein the hand section comprises a wrist section disposed at the connection of the arm section and the hand section.

25. A sling apparatus for supporting a flaccid arm of a user, the sling apparatus comprising:
   a shoulder harness removably positionable atop at least one shoulder of the user;
   a hand section removably positionable in a hand of the user, the hand section supporting weight of the arm across a surface of the hand extending at least from the second metacarpal to the fifth metacarpal;
   an arm section connecting the shoulder harness to the hand section, the arm section comprising:
      an anterior arm strap removably positionable to rest against an anterior aspect of the arm and a lateral aspect of the forearm, and
      a posterior arm strap removably positionable to rest against a posterior surface of the arm and a medial aspect of the forearm;
   a bilateral shoulder and contralateral axilla section;
   an elbow section removably positionable adjacent or at the user's elbow connected to the anterior and posterior arm straps; and
   the shoulder harness, the hand section, the anterior and posterior arm straps, and the elbow section being disposed in such a manner that the arm is supported so as to reduce shoulder subluxation and to cause the arm to substantially mimic normal movement in a dependent position.

26. The sling apparatus of claim 25 wherein the anterior arm strap comprises an elastic member.

27. The sling apparatus of claim 25 wherein the posterior arm strap comprises an elastic member.

28. The sling apparatus of claim 25 wherein the hand section is adapted to fit against a palmar surface of the user's hand.

29. The sling apparatus of claim 28 wherein the hand section comprises an object configured to the palm of the user's hand.

30. The sling apparatus of claim 25 wherein the hand section comprises at least one adjustment to control ulnar deviation.

31. The sling apparatus of claim 25 wherein the hand section comprises at least one adjustment to control radial deviation.

32. The sling apparatus of claim 25 wherein the hand section comprises a wrist section disposed at the connection of the arm section to the hand section.

33. The sling apparatus of claim 32 wherein the wrist section is removably positionable to fit against a dorsal surface of the wrist of the user.

34. The sling apparatus of claim 33 wherein the hand section comprises a wrist section disposed at a junction of the anterior and posterior arm straps where the arm straps connect to the hand section.

35. The sling apparatus of claim 32 wherein the wrist section is adjustable.

36. A sling apparatus for supporting a flaccid arm of a user in a functional position, the sling apparatus comprising:
a shoulder harness removably positionable atop a shoulder of the user;
a hand section removably positionable in a hand of the user, the hand section supporting weight of the arm across a palmar surface of the hand extending at least from the second metacarpal to the fifth metacarpal;
anterior and posterior arm straps removably positionable to fit along an arm of the user, the arm straps connecting the shoulder harness to the hand section;
a bilateral shoulder and contralateral axilla section;
an elbow support connected between the anterior and posterior arm straps and removably positionable to cradle the user's elbow;
a wrist section disposed at a junction of the arm straps where the arm straps connect to the hand section, the wrist section crossing over a wrist of the user; and
the shoulder harness, the hand section, the anterior and posterior arm straps, the elbow support, and the wrist section being disposed in such a manner that the arm is supported in a dependent position with substantially the total weight of the arm being supported from the contralateral shoulder so as to reduce subluxation in the ipsolateral shoulder, cause the arm to substantially mimic normal movement, control internal and external rotation of the arm, and provide bilateral scapular retraction, scapular depression, and thoracic spine extension.

37. The sling apparatus of claim 36 wherein the hand section comprises at least one adjustment to control ulnar deviation.

38. The sling apparatus of claim 36 wherein the hand section comprises at least one adjustment to control radial deviation.

39. A sling apparatus for supporting a flaccid arm of a user, the sling apparatus comprising:
a shoulder harness removably positionable atop at least one shoulder of the user;
a hand section removably positionable in a hand of the user, the hand section supporting weight of the arm across a surface of the hand extending at least from the second metacarpal to the fifth metacarpal;
an arm section connecting the shoulder harness to the hand section, the arm section comprising:
an anterior arm strap removably positionable to rest against an anterior aspect of the arm and a lateral aspect of the forearm, and
a posterior arm strap removably positionable to rest against a posterior surface of the arm and a medial aspect of the forearm; and
an elbow section removably positionable adjacent or at the user's elbow connected to the anterior and posterior arm straps;
wherein the shoulder harness, the hand section, the anterior and posterior arm straps, and the elbow section being disposed in such a manner that the arm is supported so as to reduce shoulder subluxation and to cause the arm to substantially mimic normal movement in a dependent position, with the wrist joint, the elbow joint, and the shoulder joint all being in compression whereby the posture, balance, and gait of the user is improved.

* * * * *